(12) United States Patent
Gabant et al.

(10) Patent No.: US 8,470,580 B2
(45) Date of Patent: Jun. 25, 2013

(54) METHOD FOR THE SELECTION OF RECOMBINATION CLONES COMPRISING A SEQUENCE ENCODING AN ANTIDOTE PROTEIN TO A TOXIC MOLECULE

(75) Inventors: Philippe Gabant, Brussels (BE); Laurence Van Melderen, Waterloo (BE); Cédric Yves Szpirer, Fleurus (BE)

(73) Assignee: Universite Libre de Bruxelles, Brussels (BE)

( * ) Notice: Subject to any disclaimer, the term of this patent is extended or adjusted under 35 U.S.C. 154(b) by 1957 days.

(21) Appl. No.: 10/468,536

(22) PCT Filed: Feb. 22, 2002

(86) PCT No.: PCT/BE02/00021
§ 371 (c)(1),
(2), (4) Date: Jan. 23, 2004

(87) PCT Pub. No.: WO02/066657
PCT Pub. Date: Aug. 29, 2002

(65) Prior Publication Data
US 2004/0115811 A1  Jun. 17, 2004

Related U.S. Application Data

(60) Provisional application No. 60/271,204, filed on Feb. 23, 2001.

(51) Int. Cl.
*C12N 1/21* (2006.01)
*C12N 15/00* (2006.01)
*C07H 21/04* (2006.01)

(52) U.S. Cl.
USPC .................. 435/252.3; 435/320.1; 536/23.1

(58) Field of Classification Search
None
See application file for complete search history.

(56) References Cited

U.S. PATENT DOCUMENTS

| | | | |
|---|---|---|---|
| 5,300,431 A | 4/1994 | Pierce et al. | |
| 5,631,153 A | 5/1997 | Capecchi et al. | |
| 5,670,370 A | 9/1997 | Molin et al. | |
| 5,855,732 A | 1/1999 | Yoshida | |
| 5,888,732 A | 3/1999 | Hartley et al. | |
| 5,910,438 A | 6/1999 | Bernard et al. | |
| 5,922,583 A * | 7/1999 | Morsey | 424/93.2 |
| 6,143,557 A | 11/2000 | Hartley et al. | |
| 6,171,861 B1 | 1/2001 | Hartley et al. | |
| 6,180,407 B1 | 1/2001 | Bernard et al. | |
| 6,270,969 B1 | 8/2001 | Hartley et al. | |
| 6,271,359 B1 | 8/2001 | Norris et al. | |
| 2005/0130308 A1 | 6/2005 | Bernard | |
| 2005/0260585 A1 | 11/2005 | Szpirer | |

FOREIGN PATENT DOCUMENTS

| | | |
|---|---|---|
| DE | 10038573 | 2/2002 |
| EP | 1111061 | 6/2001 |
| WO | WO 94/03616 | 2/1994 |
| WO | WO 97/14805 | 4/1997 |
| WO | WO 9713401 | 4/1997 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 A2 | 2/2002 |
| WO | WO 2004/022745 | 3/2004 |

OTHER PUBLICATIONS

Gotfredsen et al. Mol Microbiol. Aug. 1998, 29(4) 1065-1076.*
Hasan et al. (Gene, 56, p. 145, 1987).*
(1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Aizenman, et al. (1996) An *Escherichia coli* chromosomal "addiction module" regulated by 3', 5'-bispyrophosphate: A modayk for programmed bacterial cell death. Proc. Natl. Acad. Sci. 93:6059-6063.
Backman, K. and H.W. Boyer (1983) "Tetracycline Resistance Determined by pBR322 is Mediated by one Polypeptide." Gene 26. pp. 197-203.
Bahassi, et al. (1995) F plasmid CcdB killer protein: ccdB gene mutants coding for non-cytotoxic proteins which retain their regulatory functions. Molecular Microbiology 15(6):1031-1037.
Baubonis, et al. (1993) Genomic Targeting with Purified Cre Recombinase. Nucleic Acids Research 21(9):2025-2029.
Baum, "Tn5401, a New Class II Transposable Element from *Bacillus thuringiensis*," Journal of Bacteriology, vol. 176. No. 10, May 1994, pp. 2835-2845.
Bech et al., "Seaqence of the relB transcription unit from *Escherichia coli* and Identification of the relB gene," The EMBO Journal, vol. 4, No. 4, pp. 1059-1066, 1985.

(Continued)

*Primary Examiner* — Nancy T Vogel

(74) *Attorney, Agent, or Firm* — Knobbe, Martens, Olson & Bear LLP

(57) ABSTRACT

The present invention is related to a method for the selection of recombinant clones having integrated a gene of interest and a nucleotide sequence encoding a functional antidote protein to a toxic molecule, wherein said recombinant clones are the ones which survive following their integration into a host cell comprising in its genome a nucleotide sequence encoding said toxic molecule. The present invention is also related to a nucleic acid construct, a vector comprising said nucleic acid construct, a host cell and a cloning and/or sequencing kit for performing said method.

17 Claims, 1 Drawing Sheet

OTHER PUBLICATIONS

Bernard (1996) Positive Selection of Recombinant DNA by CcdB. BioTechniques 21(2)320-323.

Bernard, et al. (1991) The 41 carboxy-terminal residues of the miniF plasmid CcdA protein are sufficient to antagonize the killer activity of the CcdB protein. Mol. Gen Genet 226:297-304.

Bernard, P., et al. (1994) Positive-Selection Vectors Using the F Plasmid ccdB Killer Gene. Gene 148, pp. 71-74.

Bex, et al. (1983) Mini-F encoded proteins: Identification of a new 10.5 kilodalton species. The EMBO Journal, 2(11):1853-1861.

Biswas, et al. (1993) High-Efficiency Gene Inactivation and Replacement System for Gram-Positive Bacteria. J. Bacteriology 175(11):3628-3635.

Bochner, et al. (1980) Positive Selection for Loss of Tetracycline Resistance. J. Bacteriology 143(2):923-933.

Boyd (1993) Turbo Cloning: A Fast, Efficient Method for Cloning PCR Products and Other Blunt-Ended DNA Fragments into Plasmids. Nucleic Acids Research 21(4):817-821.

Bravo, et al. (1988) Killing of *Escherichia coli* cells modulated by components of the stability system ParD of plasmid R1. Mol. Gen. Genet. 215:146-151.

Bubeck, et al. (1993) Rapid Cloning by Homologous Recombination in vivo. Nucleic Acids Research 21(15):3601-3602.

Bult, "Complete Genome Sequence of the Methanogenic Archaeon, *Methanococcus jannaschii*," Science, vol. 273, Aug. 23, 1996, pp. 1058-1073.

Burns, et al. (1984) Positive Selection Vectors: A Small Plasmid Vector Useful for the Direct Selection of Sau2A-generated overlapping DNA Fragments. Gene 27:323-325.

Cole et al., "Deciphering the Biology of Mycobacterium Tuberculosis from the Complete Genome Sequence," Nature, vol. 393, Jun. 11, 1998, pp. 537-544.

Couturier, et al. (1998) Bacterial death by DNA gyrase poisoning. Trends in Microbiology 6(7):269-275.

Craine (1982) Novel Selection for Tetracycline-or Chloramphenicol-Sensitive *Escherichia coli*. J. Bacteriology 151(1):487-490.

Ebert et al. "A Moloney MLV-Rat Somatotropin Fusion Gene Produces Biologically Active Somatotropin in a transgenic pig." Molecular Endocrinology. 2:277-283, 1988.

Fleischmann et al., "Whole-Genome Random Sequencing and Assembly of Haemophilus Influenza Rd," Science, vol. 269. pp. 496-512, Jul. 28, 1995.

Gerdes (2000) Toxin-Antitoxin modules may regulate synthesis of macromolecules during nutritional stress. Journal of Bacteriology 182:561-572.

Gossen, J.A., et al. (1992) Application of Galactose-Sensitive *E.coli* Strains as Selective Hosts for LacZ Plasmids. Nucleic Acids Res. 20,p. 3254.

Gotfredsen, et al. (1998) The *Escherichia coli* relBe genes belong to a new toxin-antitoxin gene family. Molecular Microbiology 29(4):1065-1076.

Gronenborn (1978) Methylation of single-stranded DNA in vitro introduces new restriction endonuclease cleavage sites. Nature, 272:375-377.

Gronlund et al., "Toxin-Antitoxin Systems Homologous with relBE of *Escherichia coli* Plasmid P307 are Ubiquitous in Prokaryotes," Journal of Molecular Biology, vol. 285, No. 4, Jan. 29, 1999, pp. 1401-1415.

Guilfoyle, R.A., and L.M. Smith (1994) "A Direct Selection Strategy for Stotgun Cloning and Sequencing in the Bacteriophage M13." Nucleic Acids Res.22, pp. 100-107.

Hammer et al. "Genetic Engineering of Mammalian Embryos." J. Anim. Sci. 63:269-278, 1986.

Hebsgaard, S.M., et al. (1996) "Splice Site Prediction in *Arabidopsis thaliana* Pre-mRNA by Combining Local and Global Sequence information." Nucleic Acids Research, 24(17) 3439-3452.

Herrero, M., et al.(1990) "Transposon Vectors Containing Non-Antibiotic Resistance Selection markers for Cloning and Stable Chromosomal Insertion of Foreign Genes in Gram-Negative Bacteria." J. Bact. 172, pp. 6557-6567.

Holt, et al. (1993) A Novel Phage λ Replacement Cre-lox Vector that has Automatic Subcloning Capabilities. Gene 133:95-97.

Ioannou, et al. (1994) A new bacteriophage P1-derived vector for the propagation of large human DNA fragments. Nature Genetics 6:84-89.

Kaneko et al., "Sequence Analysis of the Genome of the Unicellular Cyanobacterium *Synechocystis* sp. Strain PCC6803. II.Sequence Determination of the Entire Genome and Assignment of Potential Protein-Coding Regions," DNA Research, vol. 3, pp. 109-136. 1996.

Karoui, et al. (1983) *Ham22*, a mini-F mutation which is lethal to host cell and promotes recA-dependent induction of lambdoid prophage. The EMBO Journal. 2(11): 1863-1868.

Lehnherr, et al. (1993) Plasmid Addiction Genes of Bacteriophage P1: *doc*, which cause cell death on curing of prophage, and *phd*, which prevents host death when prophage is retained. J. Mol. Biol. 233:414-428.

Liu (1989) DNA Topoisomerase poisons as antitumor drugs. Annu. Rev. Biochem. 58:351-375.

Maki, et al (1992) Modulation of DNA Supercoiling Activity of *Escherichia coli* DNA Gyrase by F Plasmid. The Journal of Biological Chemistry vol. 267(17):12244-12251.

Maloy, et al. (1981) Selection for Loss of Tetracycline Resistance by *Escherichia coli*. J. Bacteriology 145(2):1110-1112.

Manning, P.A., "Nucleotide Sequence encoding the Mannose-fucose-resistant Hemagglutinin of Vibrio Cholerae 01 and Construction of a Mutant," EMBL Sequence Database, Aug. 7, 1993. pp. 1-7.

Maxwell, et al. (1986) Mechanistic aspects of DNA Topoisomerases. Advan. Protein Chem. 38:69-107.

Messing, et al. (1977) Filamentous coliphage M13 as a cloning vehicle: Insertion of a *Hind*ll fragment of the *lac* regulatory region in M13 replicative form in vitro. Proc Natl. Acad. Sci. 74(9):3642-3646.

Miki, et al. (1984) Control of Cell Division by Sex Factor F in *Escherichia coli*. J. Mol. Biol. 174:605-625.

Miki, et al. (1984) Control of Cell Division by Sex Factor F in *Escherichia coli*. J. Mol. Biol. 174:627-646.

Moreadith et al. "Gene Targeting in Embryonic Stem Cells: The new Physiology and metabolism." J. Mol. Med. 75:208-216, 1997.

Mullins et al. "Perspective Series: Molecular Medicine in Genetically Engineered Animals." J. Clin. Invest. 98 (Suppl.): S37-S40, 1996.

Murphy, et al. (1991) pλZd39:A New Type of cDNA Expression Vector for Low Background, High Efficiency Directional Cloning. Nucleic Acids Research 19(12):3403-3408.

Nilsson, et al. (1983) An Improved Positive Selection Plasmid Vector Constructed by Oligonucleotide Mediated Mutagenesis. Nucleic Acids Research 11(22):8019-8029.

Norrander, et al. (1983 Construction of improved M13 vectors using oligodeoxynucleotide-directed mutagenesis. Gene, 26:101-106.

Ogura, et al. (1983) Mini-F plasmid genes that couple host cell division to plasmid proliferation. Proc. Natl. Acad. Sci. USA, 80:4784-4788.

pGT-N28 Vector DNA (catalog #N3728) New England Biolabs Online Catalog, Jun. 2, 1999, p. 1, www.neb.com/neb/products/nucleic/307-28.html, the whole document.

pKO Scrambler Series Gene Targeting Vectors for Knockout Mice. Stratagene Online Catalog, Jan. 1998, pp. 1-3; www.stratagene.com/cellbio/toxicology/pko.htm, the whole document.

Peakman, et al. (1992) Highly Efficient Generation of Recombinant Baculoviruses by Enzymatically Mediated Site-Specific in vitro Recombination. Nucleic Acids Research 20(3):495-500.

Roberts, et al. (1992) Definition of a Minimal Plasmid Stabilization System from the Broad-Host-Range Plasmid RK2. Journal of Bacteriology Dec. 1992:8119-8132.

Roberts, et al. (1994) The parDE operon of the broad-host-range plasmid RK2 specifies growth inhibition associated with plasmid loss. J. Mol. Biol. 18; 237 (1): 35-51.

Roca, et al. (1992) A Hit-and-Run System for Targeted Genetic Manipulations in Yeast. Nucleic Acid Research 20(17):4671-4672.

Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.

Ruiz-Echevarria, et al. (1991) Structural and functional comparison between the stability systems ParD of plasmid R1 and Ccd of plasmid. F. Mol. Gen. Genet 225:355-362.

Sadler, et al. (1980) Plasmids containing many tandem copies of a synthetic lactose operator. Gene 8:279-300.

Salmon et al., "The Antidote and Autoregulatory Functions of the F Plasmid CcdA Protein: a Genetic and biochemical Survey" Molecular and General Genetics, vol. 244, pp. 530-538. 1994.

Sambrook, et al. (1989) Molecular Cloning: A Laboratory Manual. Cold Spring Harbor Laboratory Press, Cold Spring Harbor, NY, pp. xi-xxxviii.

Sambrook, et al. (1989) Molecular Cloning: A Laboratory Manual. Cold Spring Harbor Laboratory Press, Cold Spring Harbor, NY, pp. 4.12,A.9-A.13.

Saul, et al., "Nucleotide Sequence and Replication Characteristics of RepFIB, a Basic Replicon of IncF Plasmids," Journal of Bacteriology, vol. 171,No. 5, pp. 2697-2707, May 1989.

Seamark, R.F. "Progress and Emerging Problems in Livestock Transgenesis: a Summary perspective." Repod. Fen. Dev. 6:653-657, 1994.

Smith, et al. (1985) Modification and Selection of Human Interleukin 2 Produced in Insect Cells by Baculovirus Expression Vector. Natl Acad. Sci. 82:8404-8408.

Smith, et al. (1997) The poison-antidote stability system of the broad-host-range *Thiobacilus ferroxidans* plasmid pTF-FC2. Molecular Microbiology 26(5):961-970.

Simons, R.W., et al. (1987) "Improved Single and Multicopy Lac-Based Cloning Vectors for Protein and Operon Fusions." Gene 53, pp. 85-96.

Tomb et al., "The Complete Genome Sequence of the Gastric Pathogen *Helicobacter pylori*," Nature. vol. 388, Aug. 7, 1997, pp. 539-547.

Tsuchimoto, et al. (1988) Two Genes, *pelK* and *pemI*, responsible for stable maintenance of resistance plasmid R100. J. of Bateriol., 170(4):1461-1466.

Tsuchimoto et al.,"The Stable Maintenance System pem of Plasmid R100: Degradation of PemI Protein May Allow PemK Protein to Inhibit Cell Growth." Journal of Bacteriology, vol. 174, No. 13, pp. 4205-4211, Jul. 1992.

Tsuchimoto, et al. (1993) Autoregulation by cooperative binding of the PemI and PemK proteins to the promoter region of the *pem* operon. 237:81-88.

Van Reeth, T., et al. (1998) "Positive Selection Vectors to Generate Fused Genes for the Expression of His-Tagged Proteins." Biotechniques. 25(5):898-904.

Vemet, T., et al. (1985) "A Direct-Selection Vector Derived from pColE3-CA38 and adapted for Foreign Gene Expression." Gene 34:87-93.

Wang (1985) DNA Topoisomerases. Ann. Rev. Biochem. 54:665-697.

Yanisch-Perron, et al. (1985) Improved M13 phage closing vectors and host strains: Nucleotide of the M13mp18 and pUC19 vectors. Gen, 33:103-119.

Yarmolinsky (1995) Programmed cell death in bacterial populations. Science, 267:836-837.

International Preliminary Examination Report from PCT/BE03/00045, dated Feb. 24, 2004.

International Search Report from PCT/BE00/00151, Dated May 22, 2001.

Office Action from U.S. Appl. No. 09/634,039, Dated Dec. 16, 2004.
Office Action from U.S. Appl. No. 09/634,039, Dated Jun. 29, 2005.
Office Action from U.S. Appl. No. 09/634,039, Dated Dec. 20, 2001.
Notice of Allowability from U.S. Appl. No. 08/379,614, Dated Mar. 3, 1998.
Office Action from U.S. Appl. No. 09/225,152, Dated Sep. 13, 1999.
Office Action from U.S. Appl. No. 08/379,614, Dated Aug. 27, 1996.
Office Action from U.S. Appl. No. 08/379,614, Dated Aug. 4, 1997.
Office Action from U.S. Appl. No. 09/634,039, Dated Jan. 15, 2003.
Office Action from U.S. Appl. No. 09/634,039, Dated Sep. 24, 2003.
U.S. Appl. No. 09/634,039, filed Aug. 8, 2000 by Bernard, et al.

Bernard et al. 1992 "Cell killing by the F plasmid CcdB protein involves poisoning of DNA-topoisomerase II complexes," J. Mol. Biol. 226:735-745.

Gabant et al. 1997 "Bifunctional *lacZ* α-*ccdB* genes for selective cloning of PCR products," Biotechniques 23:938-941.

Gabant et al. 1998 "Direct selection cloning vectors adapted to the genetic analysis of gram-negative bacteria and their plasmids," Gene 207:87-92.

Gabant et al. 2000 "New positive selection system based on the *parD* (*kis/kid*) system of the R1 plasmid," Biotechniques 28:784-788.

Gabant et al. 2001 "Use of poison/antidote systems for selective cloning," in Plasmid Biology 2000: International Symposium on Molecular Biology of Bacterial Plasmids, Meeting Abstracts, pp. 135-170, Plasmid 45:160-161.

Guzman et al. 1995 "Tight regulation, modulation, and high-level expression by vectors containing the arabinose $p_{BAD}$ promoter," J. Bacteriol. 177:4121-4130.

Hartley et al. 2000 "DNA cloning using in vitro site-specific recombination," Genome Res. 10:1788-1795.

Henrich et al. 1986 "Use of the lysis gene of bacteriophage ØX174 for the construction of a positive selection vector," Gene 42:345-349.

Jensen et al. 1995 "Comparison of *ccd* of F, *parDE* of RP4, and *parD* of R1 using a novel conditional replication control system of plasmid R1," Mol. Microbiol. 17:211-220.

Jensen et al. 1995 "Programmed cell death in bacteria: proteic plasmid stabilization systems," Mol. Microbiol. 17:205-210.

Kuhn et al. 1986 "Positive-selection vectors utilizing lethality of the *EcoRI* endonuclease," Gene 44:253-263.

Landy, Arthur 1989 "Dynamic, structural, and regulatory aspects of λ site-specific recombination," Annu. Rev. Biochem 58:913-949.

Muyrers et al. 2001 "Techniques: recombinogenic engineering—new options for cloning and manipulating DNA," Trends in Biochem. Sci. 26:325-331.

Pecota et al. 1997 "Combining the *hok/sok*, *parDE*, and *pnd* postsegregational killer loci to enhance plasmid stability," App. Env. Microb. 63:1917-1924.

Pierce et al. 1992 "A positive selection vector for cloning high molecular weight DNA by the bacteriophage P1 system: improved cloning efficacy," PNAS USA 89:2056-2060.

Ruiz-Echevarria et al. 1995 "A mutation that decreases the efficiency of plasmid R1 replication leads to the activation of *parD*, a killer stability system of the plasmid," FEMS Microb. Letters 130:129-136.

Schlieper et al. 1998 "A positive selection vector for cloning of long polymerase chain reaction fragments based on a lethal mutant of the *crp* gene of *Escherichia coli*," Anal. Biochem. 257:203-209.

Sierra et al. 1998 "Functional interactions between *chpB* and *parD*, two homologous conditional killer systems found in the *Escherichia coli* chromosome and in plasmid R1," FEMS Microb. Letters 168:51-58.

Trudel et al. 1996 "pGATA: a positive selection vector based on the toxicity of the transcription factor GATA-1 to bacteria," BioTechniques 20:684-693.

Yu et al. 2000 "An efficient recombination system for chromosome engineering in *Escherichia coli*," PNAS USA 97:5978-5983.

Gerdes, et al. "RNA antitoxins." (2007) Current Opinion in Microbiology, vol. 10, p. 117-124.

Pecota, et al. "Combining the hok/sok, parDE, and pnd Postsegregational Killer Loci to Enhance Plasmid Stability." (1997) Applied and Environmental Microbiology, vol. 63, p. 1917-1924.

Thisted, et al. "Mechanism of Post-segregational Killing by the hok/sok System of Plasmid R1; Sok Antisense RNA Regulates hok Gene Expression Indirectly Through the Overlapping mok Gene." (1992) J. Mol. Biol., vol. 223, p. 41-54.

Kristoffersen et al. "Bacterial Toxin-Antitoxin Gene Systems as Containment Control in Yeast Cells" Applied and Environmental Microbiology, vol. 66 No. 12, Dec. 2000, p. 5524-5526.

Gotfredsen, Marie, and Kenn Gerdes, "The *Escherichia coli relBE* genes belong to a new toxin-antitoxin gene family" Molecular Microbiology (1998) 29(4): 1065-1076.

* cited by examiner

METHOD FOR THE SELECTION OF RECOMBINATION CLONES COMPRISING A SEQUENCE ENCODING AN ANTIDOTE PROTEIN TO A TOXIC MOLECULE

RELATED APPLICATIONS

This application is the U.S. National Phase of International Application PCT/BE02/00021 filed on Feb. 22, 2002 designating the U.S. which was published in English as WO 02/066657 on Aug. 29, 2002, and which claims priority to U.S. Provisional Application No. 60/271,204 filed Feb. 23, 2001.

FIELD OF THE INVENTION

The present invention is in the field of the recombinant DNA technology.

More precisely, the present invention is related to a method, to a nucleic acid construct, to a vector and to a cell used for the selection of recombinant clones comprising a sequence encoding an antidote protein to a toxic molecule.

BACKGROUND OF THE INVENTION AND STATE Of The Art

It is possible to clone DNA inserts into vectors without ever select for recombinants and instead spend time in identification by hybridisation with radio-labelled probes, screen by restriction of small-scale preparations of plasmids or screening based on the inactivation of the alpha complementation in presence of X-Gal (blue/white screening).

These approaches used for more than one decade are not adapted to large scale cloning projects coming downstream complete genomes sequencing programs. The sequence information available has increased tremendously and will increase further in the future.

In order to assess the biological function of a coding sequence which has been identified, its corresponding gene in the genome of an organism must be specifically mutated (deleted or modified) (for instance in a knock-out mouse), which allows the study of phenotype(s) related to the mutation introduced. The specificity of the mutation is given by a targeting vector (constructed in E. coli) containing homologous recombination arms.

If the development of sequencing technologies has permitted to increase tremendously the number of sequenced genes, cloning and sub-cloning genes at large scale in order to have recombinant clones and get information about the function of the corresponding genes is still a limiting step to functional genomic programs.

Cloning and sub-cloning each gene represent the bottleneck of the "functional genomic" programs. Therefore, new cloning approaches allowing speeding up these processes are required.

Because the identification of recombinants is a limiting step, it is clear that the positive selection of recombinants is required to move from traditional approaches to high throughput cloning allowing working with thousands of genes.

Cloning vectors permitting direct selection (positive selection) of recombinant strains have been proposed (for example, see Pierce et al. 1992; Kuhn et al. 1986). However, most cloning vectors present the following drawbacks: (i) they cannot be used to incorporate large nucleotide fragments, (ii) they are not easy to manipulate and (iv) they cannot be produced by a micro-organism in a large number of copies without bringing about the death of said micro-organism.

Furthermore, traditional restriction and ligase reactions can be replaced by site-specific recombination and recombinants be selected by the replacement of the ccdB gene (a member of the poison/antidote gene family) by the insert of interest (U.S. Pat. Nos. 5,910,438, 6,180,407 and International Patent WO 99/58652).

The main advantages of the CcdB-containing vectors over the other positive selection systems are i) the small size of their selective gene (ccdb: 303 bp), ii) the fact that the vector can be amplified in a host harbouring a mutation that confers total resistance to the CcdB poison (gyrA462 resistant strain; Bernard and Couturier, 1992). Since E. coli is the host used for most molecular cloning strategies, it is important to develop new systems which can enrich and widen the range of cloning possibilities. The positive selection technology using CcdB has been used to derive new vectors adapted to peculiar purposes: PCR cloning vectors (Gabant et al., 1997), vectors adapted for bacterial genetics (Gabant et al., 1998), and recently a kid gene belonging to the CcdB family has been used to design new cloning vectors (Gabant et al., 2000 and WO01/46444).

Another example of the use of the CcdB gene is given by U.S. Pat. No. 5,888,732. This document discloses the general principle of the cloning method known as "the Gateway system". In this method, the traditional restriction and ligase reactions are replaced by site-specific recombination sites and the recombinants are selected by inactivation (by deletion) of the ccdB gene by the gene of interest. This method allows rapid and efficient transfer of all the genes from an organism from one vector to different vectors (i.e. expression vectors) by automatic sub-cloning. The resulting sub-clones maintain the orientation as well as the reading frame allowing translation fusions (for a general overview, see Hartley et al., 2000).

However, said techniques are based upon counterselectable genes requiring, the use of rpsl, tetR, sacB or ccdB counterselectable genes, which can generate a seamless second round product that carries no "scar" from the first round of recombination.

Counterselection (selection for the inactivation or deletion of a toxic gene) is typically less efficient than positive selection (acquisition of a new property) as the intended recombination is only one of the several solutions for counterselection pressure. Any mutational event that ablates expression of the counterselectable genes, will also grow under counterselection pressure.

Thus for rare genetic events (which frequency can be compared to the mutational inactivation of the counterselectable gene), candidates from second-round counter-selection strategies, need to be screened to find the intended recombination event.

In practice, it seems that the ratio of the intended to unwanted products varies widely (from <1% to 15%-85%) for reasons that are still undefined (Muyrers G. P. P., Trends in Biochemical Sciences, Vol.26, no.5, p.325-331, 2001).

Aims Of The Invention

The present invention aims to provide a new and improved method and products which do not presents the drawbacks of the state of the art and which allow an improved positive selection of recombinant clones.

A specific aim of the present invention is to provide such method and products which allow the selection of rare genetic events, especially the selection of recombinant clones having integrated long DNA fragments.

Another aim of the present invention is to propose a method and products which are not affected or less affected by the development of resistance mutations in the cells used for said positive selection.

SUMMARY OF THE INVENTION

A first aspect of the present invention is related to a method for the selection of recombinant clones having integrated a gene of interest and a nucleotide sequence encoding a functional antidote protein to a toxic molecule (to a cell, preferably a prokaryote cell), wherein said recombinant clones are the ones which survive following their integration into a host cell comprising in its genome a nucleotide sequence encoding said toxic molecule.

Another aspect of the present invention is related to products used to perform said method, especially to a nucleic acid construct comprising at least one cassette nucleotide sequence made of at least one nucleotide sequence encoding an antidote protein to a toxic molecule (to a cell, preferably to a prokaryote cell) and a gene of interest or an insertion site for said gene of interest (preferably, said insertion site being not present in the nucleotide sequence encoding the antidote protein); said cassette nucleotide sequence being disposed between a first recombination site and a second recombination site in said nucleic acid construct (said first recombination site and said second recombination site do not recombine with each other).

According to a preferred embodiment of the present invention, the antidote protein and the toxic molecule are respectively, an anti-poison protein and a poison protein. Said anti-poison or poison proteins could be wild type proteins or modified proteins which are naturally or artificially poisonous and affect one or more vital functions of a cell (preferably, a prokaryote cell) and may lead to the killing of the cell.

The antidote protein and the toxic molecule are preferably selected from the group consisting of CcdA/CcdB proteins, Kis/Kid proteins, Phd/Doc proteins, SoK/HoK proteins, RelB/relE proteins, PasB (or PasC)/PasA proteins, mazF/mazE proteins or any other couple of anti-poison/poison molecules which are or are not of plasmid origin.

The toxic molecule can also be a toxin protein being naturally or artificially toxic and affecting one or more vital functions of a (prokaryote) cell.

The protein encoded by the gene sacB (from Bacillus amylolique-faciens), the protein GpE, the protein GATA-1 and the protein Crp are other examples of such toxic molecules.

The gene sacB encodes the levan sucrase which catalyses the hydrolysis of sucrose into products which are toxic for E. Coli (Pierce et al. *Proc. Natl. Acad. Sci.*, Vol. 89, N°6 (1992) p. 2056-2060). The protein GpE encodes the E genes from the bacteriophage φX174 which includes six unique restriction sites and encodes gpE and which causes lysis of *E. Coli* cell (Heinrich et al., *Gene*, Vol. 42 n°3 (1986) p. 345-349). The protein GATA-1 has been described by Trudel et al. (*Biotechniques* 1996, Vol. 20(4), p. 684-693). the protein Crp has been described by Schlieper et al. (*Anal. Biochem.* 1998, Vol. 257 (2), p. 203-209).

The antidote proteins to said toxic molecule are any protein able to reduce or suppress the effect of the corresponding toxic molecule on a cell (preferably a prokaryotic cell), when said toxic molecule is produced by said cell.

According to another embodiment of the present invention, the nucleotide sequence encoding the antidote protein is a first nucleotide fragment encoding an inactive antidote protein, which can be rendered active (functional) following correct integration of the gene of interest in the cassette sequence.

Preferably, the cassette sequence present in the nucleic acid construct according to the invention comprises also promoter/operator sequences in order to obtain the expression of the antidote protein which can be expressed constitutively or following the insertion of the gene of interest (insert) or by a recombination event.

For instance, the antidote activity can be achieved when the gene of interest (insert) brings a sequence comprising a transcriptional and/or translation signal that allows the expression of the antidote protein or when the gene of interest integrates another antidote sequence, a portion of it or its C-transcriptional or translation signal through insertion or by a recombination event.

By said mechanism, the correct insertion of the gene of interest inside the nucleic acid construct can also be advantageously selected.

Said gene of interest may also further comprise a promoter/activator sequence which allows or improves the expression of said antidote protein or comprises a second nucleotide fragment which will complement the first nucleotide fragment of said antidote protein in order to render said antidote protein functional (active against the toxic molecule).

According to a further embodiment of the present invention, the insertion site of the gene of interest is a cloning site, such as a recombination site or a nucleotide sequence specifically cleaved by one or more restriction enzymes.

Advantageously, the insertion site for said gene of interest is comprised in a nucleotide sequence encoding a toxic molecule, preferably a poison protein. Therefore, the nucleic acid construct according to the invention is based upon firstly, a negative selection which following the integration of the gene of interest into the nucleotide sequence encoding the toxic molecule inactivates said sequence and secondly a positive selection which allows thereafter, the expression of an antidote protein.

This double selection allows, advantageously, an improved selection of recombinant clones with rare genetic events, such as the integration of a very long DNA fragments, inside the nucleic acid construct according to the invention.

In the nucleic acid construct according to the invention, the first and the second recombination sites, recognised by recombinase(s), are preferably att phage λbased sites (specific recombination sites such as the ones described by Ptashne M. et al. (Genetic switch, Cell Press, Cambridge, 1992). Preferably, said att sites are integrated into a nucleic acid construct according to the invention by the method described by Landy A. et al. (Annual Review, Biochemistry, Vol.58, p.913, 1989)).

However, other types of recombination sites can be also integrated into the nucleic acid construct according to the invention.

Another aspect of the present invention is related to a vector (an autonomously replicating vector such as a plasmid, a bacteriophage, a virus, a cationic vesicle or any other type of vector) comprising the nucleic acid construct according to the invention.

A preferred embodiment of the present invention is related to a vector donor, DNA molecule comprising a first DNA segment and a second DNA segment, said first or second DNA segment containing as selectable marker at least one nucleotide sequence encoding an antidote protein to a toxic molecule, and wherein said first and second DNA segment is flanked by at least a first and second recombination site, which do not recombine with each other.

Said selectable marker in the vector DNA molecule according to the invention may also comprise at least one inactive fragment of the antidote sequence and a functional selectable marker is obtained, when recombining across said first and second recombination sites with a further DNA segment comprising the inactive fragment of said selectable marker (other fragment of the antidote sequence).

In the vector donor DNA molecule, the recombination sites are the above-described recombination sites, preferably selected from the group consisting of the various recombination sites such as the ones described in the U.S. Pat. No. 5,888,732.

The vector donor DNA molecule according to the invention is advantageously combined in a kit of parts (preferably, in a cloning kit) with an insert donor DNA molecule, said insert donor DNA molecule comprising the first DNA sequence flanked by the first recombination site and a second recombination site which do not recombine with each other. The characteristics of said insert DNA molecules are the ones described in the U.S. Pat. No. 5,888,732 and patents WO99/21977, WO01/31039, WO01/42509 incorporated herein by reference.

Another aspect of the present invention is related to a cell, possibly integrated in the above-mentioned kit, preferably a prokaryotic host cell for the vector or the nucleic acid construct according to the invention, said cell having incorporated in its chromosomal DNA, at least one (preferably, at least two or more) nucleotide sequence(s) encoding the toxic molecule (for which the nucleotide sequence present in the nucleic acid construct is encoding an antidote), the expression of said toxic molecule being negatively repressed (controlled), preferably by a transcriptional and/or translation repressive tool, for instance, by adding to said nucleotide sequence encoding the toxic molecule a repressive promoter/operator nucleotide sequence which allows a transcriptional and/or translation repressive control of said protein poison and avoid the death of the cell.

However, said repressive control can be removed by adding or suppressing the addition of a specific compound to the cell (i.e.: a saccharide), Which allows the expression of the toxic molecule by the cell.

Furthermore, the activity of the toxic molecule could be also conditional (for example, by introducing in the cell a thermosensitive allelle or a specific amber mutation suppression).

Furthermore, the cell could comprise also an antidote which is expressed in specific conditions and is able to block the deleterious effect of said toxic molecule in the cell.

Preferably, the cell according to the invention is an *E. coli* cell which has the deposit number LMGP-21399.

Said cell was deposited in the Laboratorium voor Microbiologie—Universiteit Généralement, K. L. ledeganckstraat 35, B-9000 Gent, Collection of the Belgian Coordinated Collection of micro-organisms, BCCM, under no. LMGP-21399, on the date of Feb. 15, 2002). Said deposit has been made in accordance with the provision of the Budapest treaty regarding the international recommission of the deposit of microorganisms.

Another aspect of the present invention is related to the use of said products for the selection of recombinants and to a method for selecting recombinant clones comprising the step of providing a cassette sequence in the nucleic acid construct or the vector according to the invention or inserting a gene of interest in the insertion site provided in said cassette sequence, transform the cell according to the invention with the nucleic acid construct or the vector according to the invention and selecting recombinant cell clones which survive.

The present invention will be described in more details in the following non-limiting example.

DETAILED DESCRIPTION OF THE INVENTION

Description of Plasmids and Strains

Figure 1:
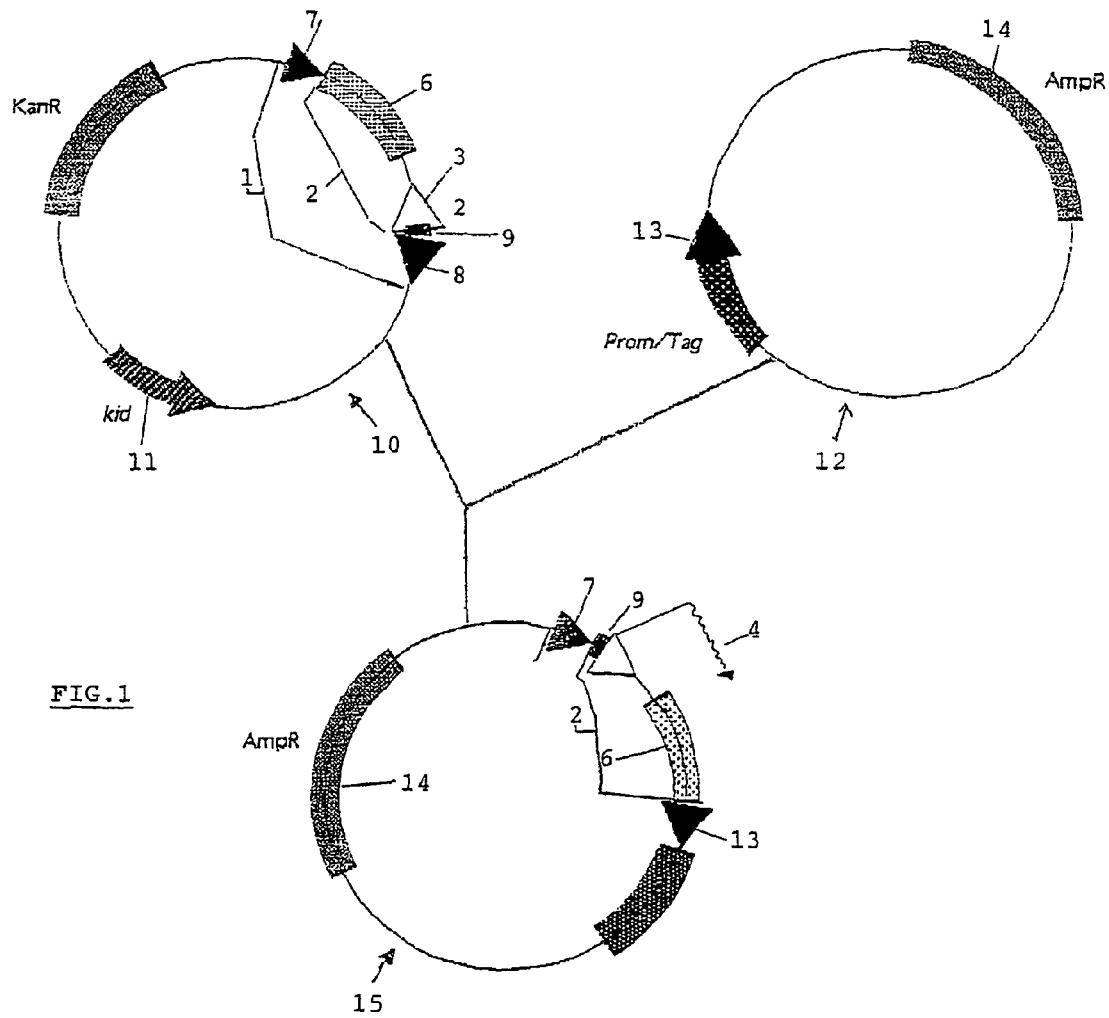
FIG. 1 depicts a nucleic acid construct 1 according to the invention.

The FIG. 1 describes a nucleic acid construct 1 according to the invention which comprises a cassette nucleotide sequence 2 made of a nucleotide sequence 3, encoding an antidote protein 4 to a toxic molecule 5 and a gene of interest 6 or an insertion site for a gene of interest 6, and a promoter/operator sequence 9; said cassette sequence 2 being disposed between a first recombination site 7 and a second recombination site 8, said first and second recombination site(s) 7,8 do not recombine with each other.

Said nucleic acid construct 1 is advantageously integrated into a vector which is an insert donor DNA vector 10 comprising a further selectable marker 11. Said insert DNA donor vector 10 can be combined with an insert acceptor DNA vector 12, comprising a recombination site 13 and another selectable marker 14, said insert donor DNA vector 10 and said insert acceptor vector or molecule 12 after recombination form the recombinant vector 15 according to the invention. The correct recombination orientation will be selected by using the characteristics of the selective marker 11 and by using a bacterial strain expressing in its chromosome one or more genetic sequence(s) encoding the toxic molecule 5.

In the present case, the nucleotide sequence encoding an antidote protein 4 is a nucleotide sequence encoding the CcdA protein, which is the antidote to the toxic molecule 5 (CcdB protein), expressed by the bacteria.

The first selectable marker 11 presented in the insert donor DNA vector 10 is the protein poison kid and the second selectable marker 14 is a genetic resistance to an antibiotic (ampicyline).

Advantageously, the insert donor DNA vector 10 could be amplified in a bacteria which is resistant to the activity of the first selectable marker 11, for instance, a bacteria expressing the antidote protein kis to the protein poison kid.

Such bacteria comprising constitutively the kis sequence is described in the document WO01/46444 and protected by the deposit number LMGP-19171.

Another aspect of the present invention concerns the strain host cell 20 wherein the selection of the recombinant clones is performed.

The preferred strain is an *Escherichia coli* strain CYS10, which is a derivative of DH10B strain (mcrA Δ(mrr-hsdRMS-mcrBC)Φ80lacZdM15 ΔlacW74 endA1 recA1 deoR Δ(ara, leu)7697 araD139 ga/U ga/K nupG rpsL, commercialised by Invitrogen). This strain carries a ccdb poison gene 21 under the control of the $P_{tac}$ promoter 22 in the dcm gene of the chromosome, a defective λ expressing the Red and Gam functions under the control of λ PERFLUOROCARBON LIQUID promoter and the temperature sensitive CI857 repressor (descritpion of this system: Yu et al., 2000, PNAS 97:5978-5983) and two plasmids (Pulb3566 23 n Psc101Laclq 24). The pULB3566 plasmid 23 produces the CcdA antidote 3 under the control of the $P_{bad}$ promoter and carries the ampicilline resistance gene. The Psc101 laclq 24 plasmid produces the Laclq repressor and carries the spectinomycine resistance gene. The Ptac promoter 22, controlling the expression of the ccdB poison gene, is repressed by the LacIq protein, and is induced by the addition of IPTG 26 (isopropyl β-D thiogalactoside, $C_9H_{18}O_5S$, Roche; 0,5 mmole/liter) in the culture media. However, even in the presence of the LacIq protein, the Ptac promoter 22 is not completely repressed causing a residual expression. The Pbad promoter, controlling the expression of the ccda antidote gene 3, is completely repressed in the absence of arabinose 25 and induced by the addition of arabinose 25 (1%) in the culture media (Guzman et al., 1995, Journal of bacteriology, Vol.177, p.4121-4130).

Due to the temperature sensitive DI857 repressor, the strain grows only at 30° C. Due to the presence of ccdB in the chromosome, the strain grows only in the presence of arabinose allowing the production of the CcdA antidote. Consequently, the strain grows at 30° C., in LB medium and in presence of arabinose (1%).

| Media | CcdA production | CcdB production | CYS10 strain at 30° C. |
|---|---|---|---|
| LB + Ara(1%) | Yes, induced | Yes, residual | Growth |
| LB | No, repressed | Yes, residual | No growth |
| LB + IPTG(0.5 mM) | No, repressed | Yes, induced | No growth |
| LB + Ara(1%) + IPTG(0.5 mM) | Yes, induced | Yes, induced | Growth |

Figure 2:
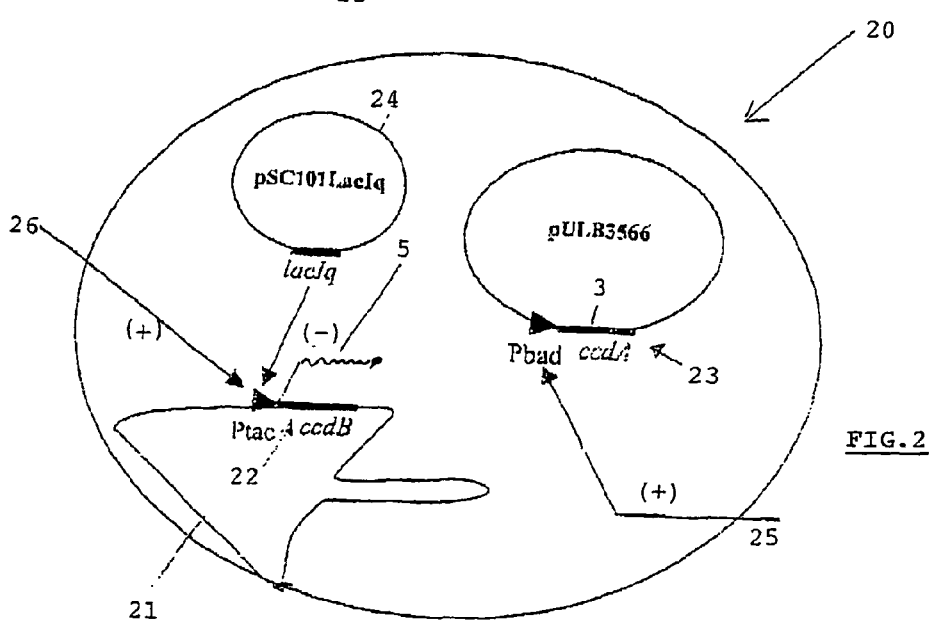
FIG. 2 is schematic representation of the CYS10 construct.

The schematic representation of the CYS10 construction is presented in FIG. 2.

However, the characteristics of said bacterial strain can be improved by the deletion of thermosensitive characteristic and by the introduction of additional genetic sequences encoding more toxic molecules in order to reduce or avoid the selection of mutants which are resistant to the activity of said toxic molecule (ccdB production).

The invention claimed is:

1. A nucleic acid construct comprising a cassette sequence disposed between a first recombination site and a second recombination site, said cassette sequence comprising a first nucleotide sequence encoding a first portion of an antidote protein to a poison protein wherein said first portion of said antidote protein is inactive and a site for the integration of a DNA insert, said antidote protein being reconstituted as functional antidote protein to the poison protein following insertion of a second nucleotide sequence encoding a second portion of said antidote protein into the cassette, wherein the antidote and poison proteins are selected from the group consisting of the following coupled proteins: CcdA/CcdB protein, Kis/Kid protein, Phd/Doc protein, RelB/RelE protein, PasB/PasA protein, PasC/PasA protein and mazE/mazF protein.

2. The nucleic acid construct according to claim 1, wherein the first recombination site and the second recombination site are att phage λ based sites.

3. A vector which comprises the nucleic acid construct according to claim 1.

4. The vector according to claim 3, which is an autonomously replicating vector.

5. A cloning and/or sequencing kit comprising the nucleic acid construct of claim 1 or a vector which comprises said nucleic acid construct, said cloning and/or sequencing kit further comprising or a recombinant prokaryotic host cell having incorporated in its chromosomal DNA a recombinant nucleotide sequence encoding a poison protein, wherein the toxicity of said poison protein can be overcome by a functional version of the antidote protein present in inactive form in said nucleic acid construct or vector and wherein said poison protein is selected from the group consisting of CcdB, Kid, Doc, RelE, PasA and MazF.

6. The vector of claim 4, wherein said vector is a viral or a plasmid vector.

7. The nucleic acid construct according to claim 1, wherein the first and second recombination sites are recognized by a recombinase.

8. The kit according to claim 5, wherein the first and second recombination sites in said nucleic acid construct of claim 1 or said vector which comprises said nucleic acid construct are recognized by a recombinase.

9. A vector comprising a cassette sequence comprising a first nucleotide sequence encoding a first portion of an antidote protein to a poison protein wherein said first portion of said antidote protein is inactive and a site for integrating a DNA insert, said antidote protein being reconstituted as an functional antidote protein following integration of the DNA insert into the cassette sequence, wherein said DNA insert comprises a second nucleotide sequence encoding a second portion of said antidote protein and wherein the antidote and poison proteins are selected from the group consisting of the following coupled proteins: CcdA/CcdB protein, Kis/Kid protein, Phd/Doc protein, RelB/RelE protein, PasB/PasA protein, PasC/PasA protein and mazE/mazF protein.

10. The vector according to claim 9, which is an autonomously replicating vector.

11. A recombinant prokaryotic cell, which comprises the vector of claim 9, and which has incorporated in its chromosomal DNA a recombinant nucleotide sequence encoding said poison protein.

12. The nucleic acid construct according to claim 1, wherein the nucleotide sequence comprising the insert comprises a promoter/operator sequence.

13. A nucleic acid construct comprising a cassette sequence with a first nucleotide sequence encoding a first portion of an antidote protein to a poison protein wherein said first portion of said antidote protein is inactive and a site for the insertion of a DNA insert, said antidote protein being reconstituted as a functional antidote protein to the poison protein following integration of a second nucleotide sequence encoding a second portion of said antidote protein into the cassette sequence, wherein the antidote and poison proteins are selected from the group consisting of the following coupled proteins: CcdA/CcdB protein, Kis/Kid protein, Phd/Doc protein, RelB/RelE protein, PasB/PasA protein, PasC/PasA protein and mazE/mazF protein.

14. The nucleic acid construct of claim 1, wherein said DNA insert brings a sequence comprising a transcriptional and/or translational signal that allows the expression of the antidote protein or wherein the DNA insert integrates another nucleotide sequence encoding the antidote protein, a portion of the antidote protein or a C-terminal, transcriptional or translational signal of the antidote protein.

15. The vector of claim 9, wherein said DNA insert brings a sequence comprising a transcriptional and/or translational signal that allows the expression of the antidote protein or wherein the DNA insert integrates another nucleotide sequence encoding a C-terminal, transcriptional or translational signal of the antidote protein.

16. The nucleic acid construct of claim 13, wherein said DNA insert brings a sequence comprising a transcriptional and/or translational signal that allows the expression of the antidote protein or wherein the DNA insert integrates another nucleotide sequence encoding a C-terminal, transcriptional or translational signal of the antidote protein.

17. The recombinant prokaryotic cell of claim 11, wherein the transcription of said recombinant nucleotide sequence encoding said poison protein is under the control of a repressible promoter.

* * * * *